United States Patent [19]

Ellinger

[11] 4,026,414

[45] May 31, 1977

[54] APPARATUS FOR TESTING TOPS OF CONTAINERS FOR DAMAGE

[75] Inventor: Bernd Ellinger, Regensburg, Germany

[73] Assignee: Hermann Kronseder Maschinenfabrik, Neutraubling, Germany

[22] Filed: Jan. 7, 1976

[21] Appl. No.: 647,300

[30] Foreign Application Priority Data

Jan. 18, 1975 Germany .......................... 2501975

[52] U.S. Cl. .................... 209/111.7 R; 250/223 B; 250/578; 356/240
[51] Int. Cl.² ......................................... B07C 5/10
[58] Field of Search ................ 209/111.5, 111.7 R, 209/111.7 T; 250/223 B, 578, 227; 356/239, 240, 198, 237

[56] References Cited

UNITED STATES PATENTS

| | | | |
|---|---|---|---|
| 3,500,053 | 3/1970 | Calhoun | 250/223 B |
| 3,509,996 | 5/1970 | Malik | 250/223 B X |
| 3,631,255 | 12/1971 | Gender et al. | 250/223 B |
| 3,687,559 | 8/1972 | Fischer | 250/223 B X |
| 3,827,812 | 8/1974 | Heimann | 250/223 B X |
| 3,877,821 | 4/1975 | Price et al. | 356/237 |
| 3,894,806 | 7/1975 | Remy et al. | 250/223 B X |
| 3,980,890 | 9/1976 | Heckrodt et al. | 250/223 B X |

Primary Examiner—Robert B. Reeves
Assistant Examiner—Joseph J. Rolla
Attorney, Agent, or Firm—Joseph P. House, Jr.

[57] ABSTRACT

Inspection apparatus for detecting defects in the rim of bottles or containers includes a light sensing head made up of a mosaic of thirty to forty light sensors in the form of circular ring sectors supported on a platen and arranged around a central aperture. The sensing head is located above the bottles and inspects the bottles as they are conveyed through the inspection zone. A light source provides a beam through the central aperture which floods the mouth of the bottle with the light being reflected upwardly from the bottle rim to the various sensors which simultaneously sense light reflected from the entire bottle rim. The light sensor outputs are individually monitored and circuitry is provided to activate a bottle sorting device when an amplified output signal from any of the cells varies a predetermined amount from a normal signal value. The large number of sensors and individual monitoring of these devices provides a high sensitivity for accurate detection of flaws or defects in the rim of the bottle.

15 Claims, 11 Drawing Figures

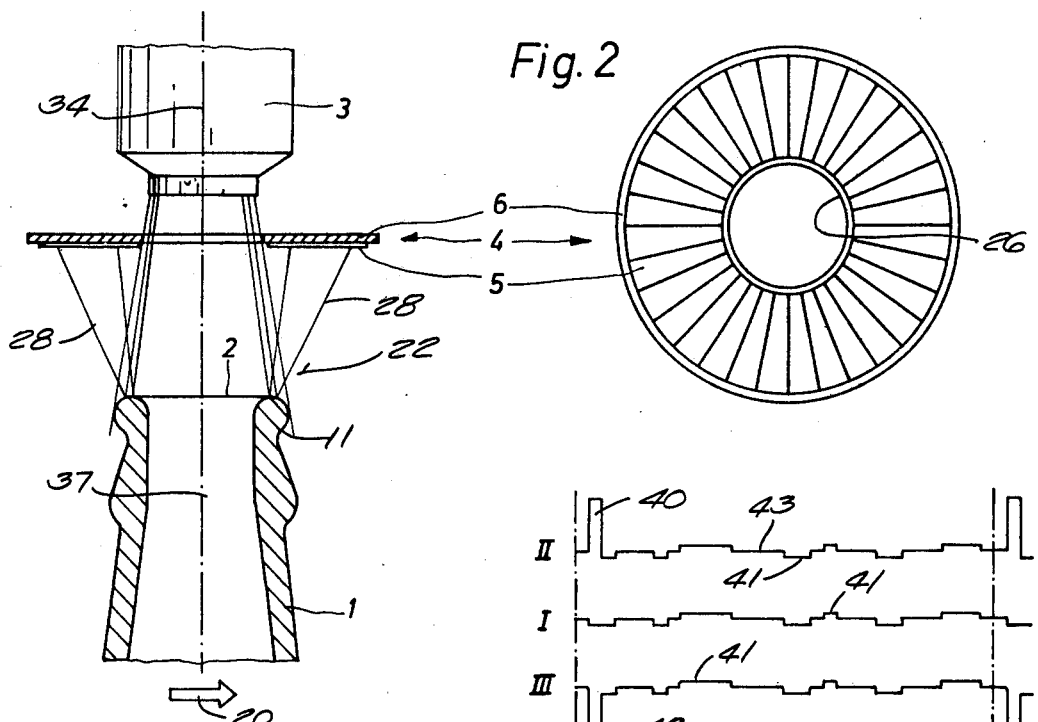
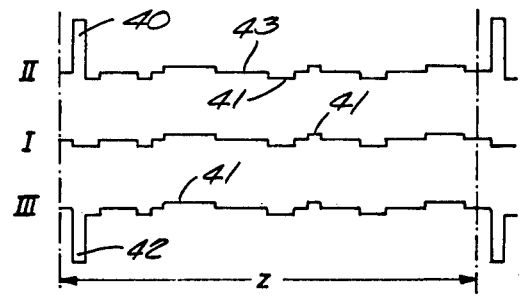
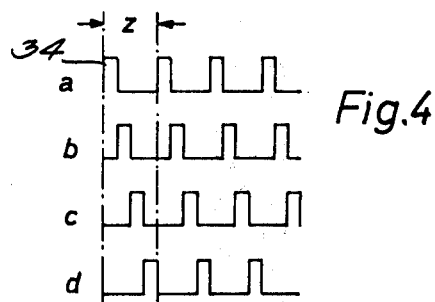
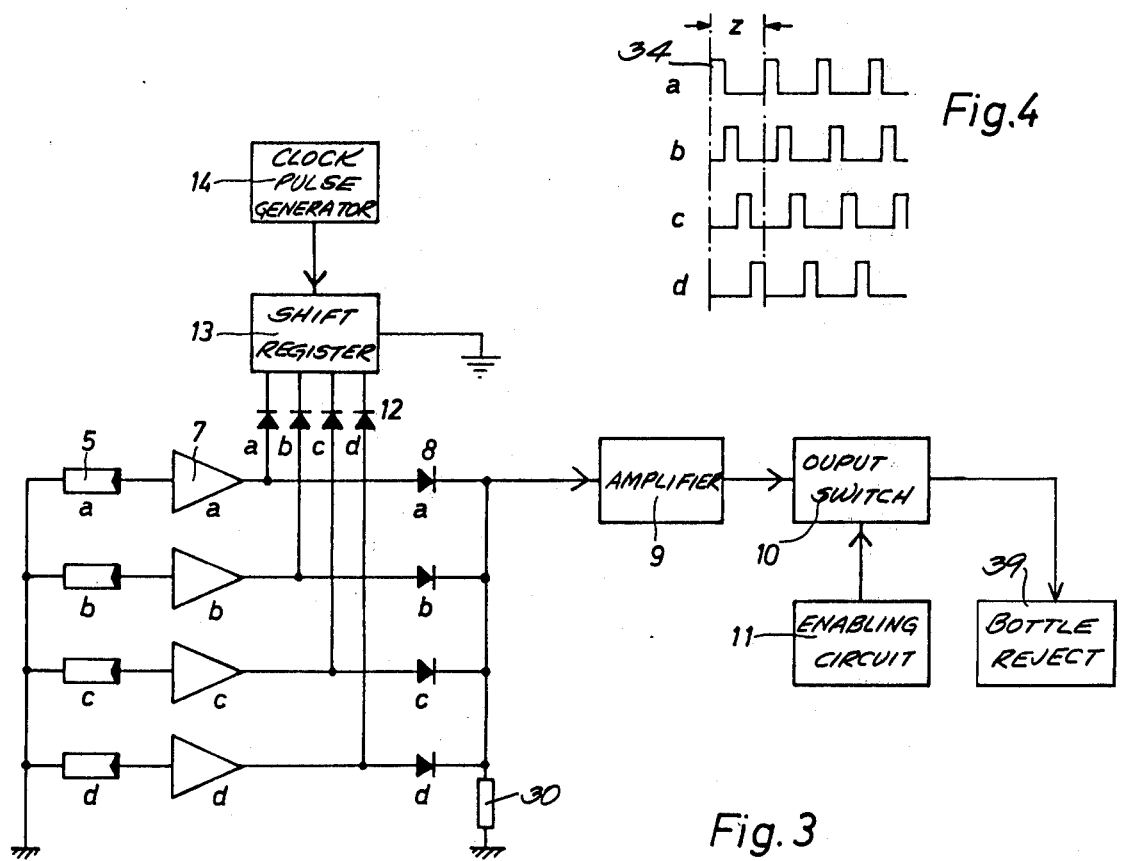

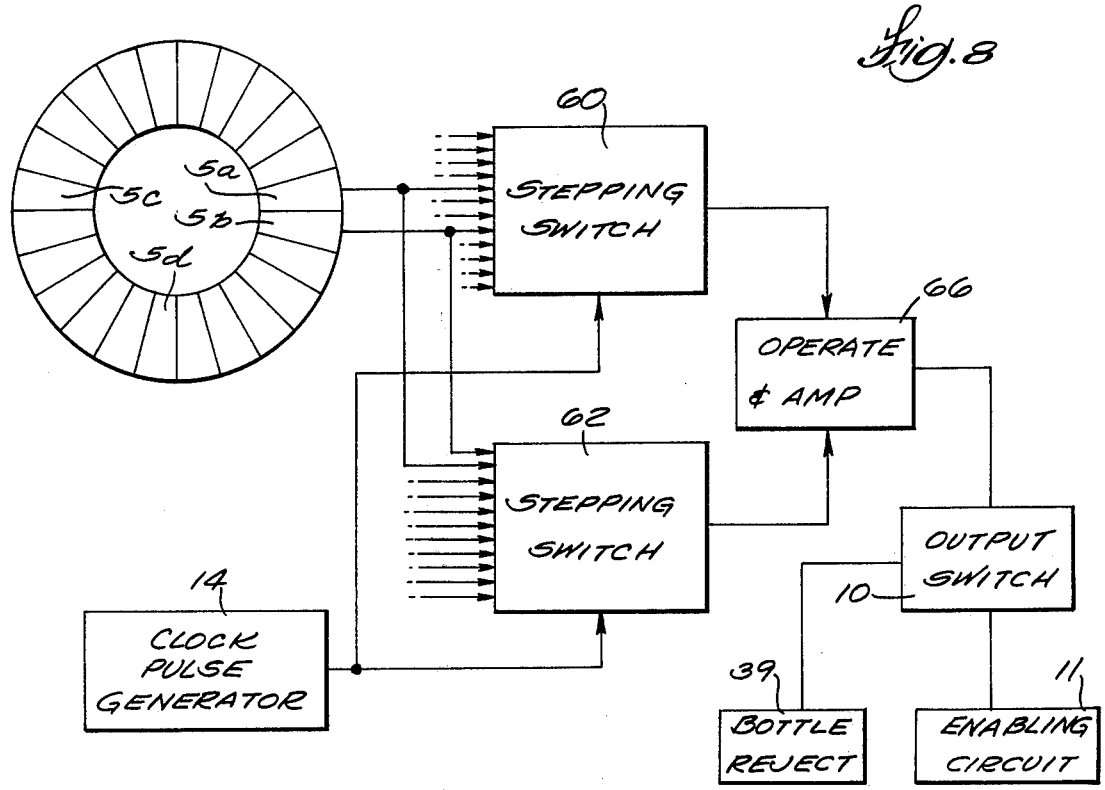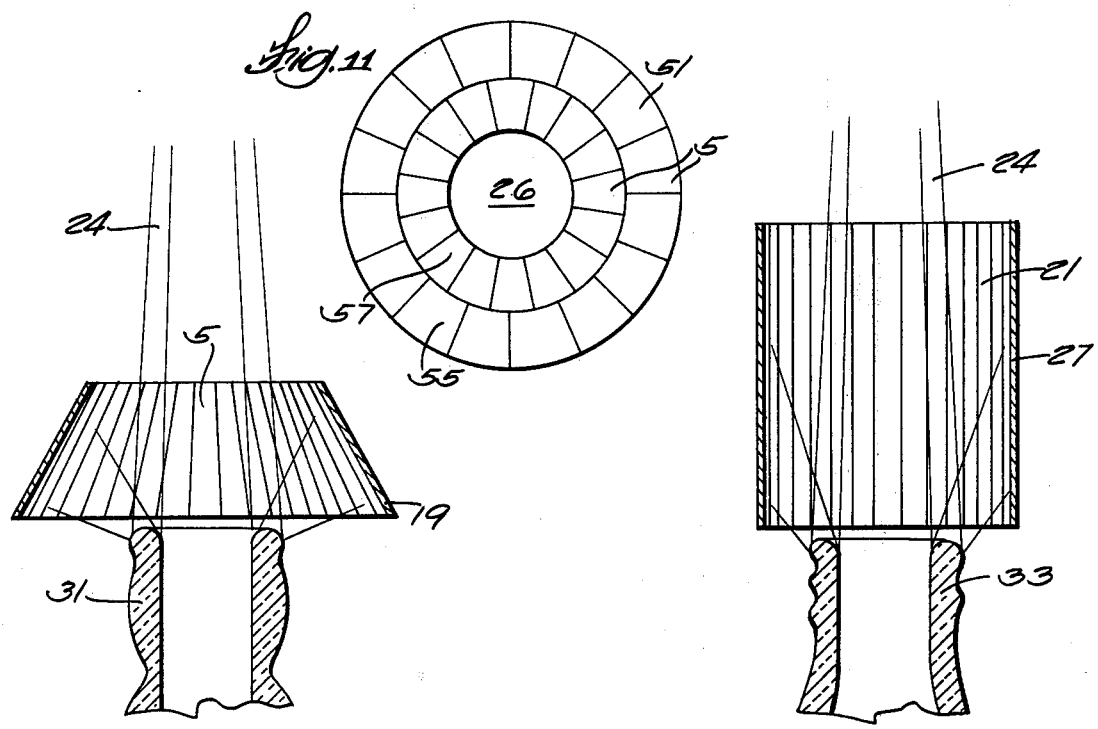

APPARATUS FOR TESTING TOPS OF CONTAINERS FOR DAMAGE

BACKGROUND OF THE INVENTION

Prior art optical container inspection systems include apparatus in which a light sensor rotates around the center axis of the mouth of the container for a rotary scan of the rim or mouth of the container. U.S. Pat. No. 3,349,906 is illustrative of a rotating scanning head. The mechanical problems associated with movement of a photo device, limit the speed and accuracy of apparatus of this type. Wear of the bearing and drive mechanism and difficulty in transmission of signals from the rotating sensor minimize the effectiveness of such a system.

SUMMARY OF INVENTION

The prsent invention provides inspection apparatus which includes a stationary light sensing head and a stationary light source which are adapted for in-line inspection of containers moving along a conveyor path to provide fast and reliable flaw and defect detection without the problems associated with rotating scanning heads. The sensing head has thirty to forty light sensors such as solar cells which in one embodiment have light receiving surfaces in the shape of circular ring sectors which are arranged around a central aperture. The sensing head can be flat, conical, or cylindrical in shape, depending on which portion of the bottle mouth is to be inspected. A flat sensing head is adequate for inspection of a bottle mouth rim and the conical or cylindrical shaped sensing heads are preferable for inspecting screw threads on the bottle mouth.

A light source provides a beam through the aperture to flood the entire bottle mouth rim. Light reflected from the entire rim is simultaneously sensed by all the sensors in the sensing head. The substantial number of sensors enables inspection of the complete bottle rim with a stationary sensing head and light source. Individual pre-amplifiers for each sensor provide high sensitivity for detecting minor flaws.

The sensors are individually monitored by a circuit so that an output signal from any one of the sensors which is above or below a preselected normal signal value caused by the reflection from a defect-free bottle will cause energization of an output switch to actuate a container sorting device or reject mechanism to separate the defective bottle from the conveyor. Flaws which cause either increased or decreased light reflection are sensed and provide actuation of the sorting mechanism.

The sensors are desirably carried on a platen with an individual pre-amplifier for each sensor, also supported on the platen. Variable resistors for each of the individual sensors can also be carried on the plate to enable adjustment to provide uniform outputs for each cell.

Further objects, advantages and features of the invention will become apparent from the following disclosure.

DESCRIPTION OF DRAWINGS

FIG. 1 is a fragmentary elevational view in partial section of a bottle neck and sensing head in accordance with the invention.

FIG. 2 is a plan view of the sensing head shown in FIG. 1.

FIG 3 is a schematic diagram of one embodiment of the monitoring circuit.

FIG. 4 is a schematic view of pulses produced by a clock pulse generator shown in FIG. 3.

FIG. 5 is a diagram of typical output signals produced by the circuit of FIG. 3.

FIG. 8 is a schematic diagram of a further modified embodiment of a circuit for monitoring the output of the sensors.

FIG. 9 is a sectional view of a modified embodiment of a sensing head with the light sensors supported on the inside surface of a conical carrier.

FIG. 10 is a sectional view of a further modified embodiment of a sensing head with the sensors supported on the inside surface of a cylindrical carrier.

FIG. 11 is a plan view of a further embodiment of a sensing head with the sensors arranged in two concentric rings.

DESCRIPTION OF THE PREFERRED EMBODIMENT

Figure 6:
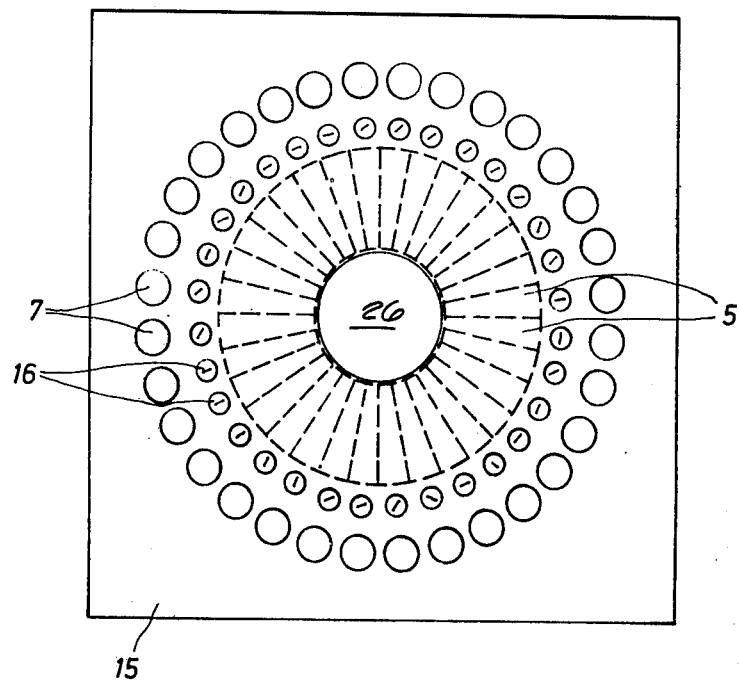
FIG. 6 is a plan view of a further embodiment of the sensing head of the invention in which the sensors are supported on a platen and which includes a pre-amplifier and a voltage adjustment device for each sensor.

Although the disclosure hereof is detailed and exact to enable those skilled in the art to practice the invention, the physical embodiments herein disclosed merely exemplify the invention which may be embodied in other specific structure. The scope of the invention is defined in the claims appended hereto.

FIG. 1 shows a bottle neck 1 with a rim 2 for a bottle mouth 11. The bottle 1 is representative of a series of bottles being conveyed along a path 20, by conveying apparatus (not shown). The bottle 1 is located in an inspection zone 22 through which each bottle moves in sequence.

The inspection apparatus includes a stationary light source 3 which provides a beam of light 24 which is slightly larger in diameter than the rim of the bottle mouth 11. Thus, the rim of the bottle remains in the light beam during the inspection cycle, although some minor movement of the bottle occurs as a result of movement. The light beam 24 projects through an aperture 26 in a sensing head 4 which is in the form of a ringshaped platen 6.

The sensing head 4 of FIGS. 1, 2 and 6 includes a plurality of light sensors or photocells 5 which have a light sensitive surface in the form of circular ring sectors which are circumferentially arranged around the aperture 26. The light rays 28 from the bottle rim 2 impinge on the sensors 5. The light source 3 provides equal and continuous illumination along the bottle rim 2 to thus, provide a uniform intensity of reflection for a normal rim of each of the solar sensors. With the light source concentrically located with respect to the sensing head, the reflected light is approximately centered on the solar sensors. The sensing head 4 has a diameter substantially larger than the bottle rim so that the cone of reflected light 28 will be received by the sensors even though there is bottle movement during the inspection cycle.

FIG. 9 shows a modified form of a sensing head in which the solar sensors 5 are arranged and supported on the inside surface of a conical-shaped carrier 19 which provides a light receiver which is advantageous for inspecting the sides 31 of the mouth in addition to the rim.

FIG. 10 shows a sensing head in a cylindrical shape with the sensors 21 arranged around the inside surface of a cylinder 27. The FIG. 10 embodiment is desirably used for inspecting threads 33 on the container as well as the rim.

FIG. 11 illustrates a sensing head 51 in which the sensors 5 are arranged in two concentric rings 55 and 57 around a central aperture 26.

In accordance with the invention, a circuit is provided for monitoring the outputs of each of the sensors 5 to actuate a bottle sorting device 39 if the output signals from any one of the sensors 5 indicates a bottle flaw or defect.

FIG. 3 shows one embodiment of a monitoring circuit connected to the sensors 5. For purposes of illustration, FIG. 3 shows only four sensors 5a, b, c and d which are representative of a few of the many sensors contained on the sensing head 6.

In the circuit shown in FIG. 3, the outputs of each of the sensors are individually and sequentially scanned and if the amplified output from any one cell is above or below a predetermined value for a normal bottle rim, an output switch 10 is enabled to actuate a bottle sorting device 39. The sensors 5a, b, c, and d each have one terminal commonly grounded and another terminal connected to each of the pre-amplifiers 7a, b, c and d. The outputs of pre-amplifiers 7a, b, c and d are connected to a common load resistor 30 through diodes 8a, b, c and d.

The outputs of the pre-amplifiers 7a, b, c and d are also coupled to a shift register 13 through diodes 12a, b, c and d. The outputs of the amplifiers 7a, b, c and d are thus, grounded through the shift register 13. The outputs of the pre-amplifiers 7a, b, c and d are sequentially enabled to sequentially provide output signals from the sensor 5 to the amplifier 9 by a clock pulse generator 14 which provides successive pulses 34 as shown in FIG. 4. When the pulse 34 (FIG. 4) is applied the shift register 13, the output of the pre-amplifier 7a is decoupled from ground or enabled and thus, the output from sensor 5a is applied to an amplifier 9 which provides an amplified pulse to an output switch 10. Switch 10 can be a relay or gate-operated switch circuit or the like for actuating a sorting device 39. As shown in FIG. 4, the amplifiers 7a, b, c and d are sequentially enabled and coupled to amplifier 9 by the series of pulses 34 in inspection cycle Z, cycle Z representing the scanning cycle for all sensors for one bottle. The cycle Z commences just prior to coincidence or register of the bottle centerline 37 with the centerline 34 of the light source and ends a short time after the bottle centerline 37 moves from coincidence with the light source centerline 34. When using forty sensors 5 in the sensing head, an appropriate scanning cycle Z is one millisecond with the clock 14 providing 40,000 scanning pulses per second. Thus, the inspection apparatus is capable of operating with high bottle movement rates through the inspection zone 22.

The output switch 10 has adjustment capability so that it will only activate the sorting device when a signal is received which is a preselected value above or below a pre-determined signal level for a normal bottle. The switch 10 can be adjusted so that small fluctuations in signal above or below the preselected normal signal level caused by seams in the glass or slight deviations from an ideal mouth shape, will not cause actuation of the bottle sorting device 39.

The FIG. 5 shows three voltage signals to the amplifier 9. Curve I shows small variations caused by seams or deviations from a perfect mouth shape. The output switch 10 is adjusted so that small fluctuations 41 in voltage from a normal level 43 do not activate the bottle sorting device 39. Curves II and III show significant pulses 40 and 42 above and below the normal level 41 which have sufficient magnitude to actuate the output switch 10. The peaks 40, 42 could, for instance be caused by cracks or irregulatities in the rim 2.

The monitoring circuit in FIG. 3 also includes an enabling circuit 11 for the output switch 10. The enabling circuit operates in response to the presence of a bottle in the inspection zone and only enables the output switch to actuate the sorting sensor at the appropriate time. Thus, pulses caused by the sensors during the interval when a bottle is not centered in the inspection zone will be disregarded by the output switch 10. A photocell, microswitch or other sensor can be employed with the enabling circuit to sense the presence of a bottle in the sensing zone, and enable the output switch 10 only when a bottle is being inspected. The output switch enabling circuit 11 could also be operated by a timer.

FIG. 6 shows a platen 15 which contains 32 sensors 5 arranged around aperture 26. The plate 15 also carries a pre-amplifier 7 for each of the solar sensors and a voltage adjusting device such as a variable resistor 16 so that the output voltages of all sensors 5 can be adjusted to provide the same output voltage. The platen 15 can also carry the printed circuitry for the circuits shown in FIGS. 3, 7 and 8.

Figure 7:
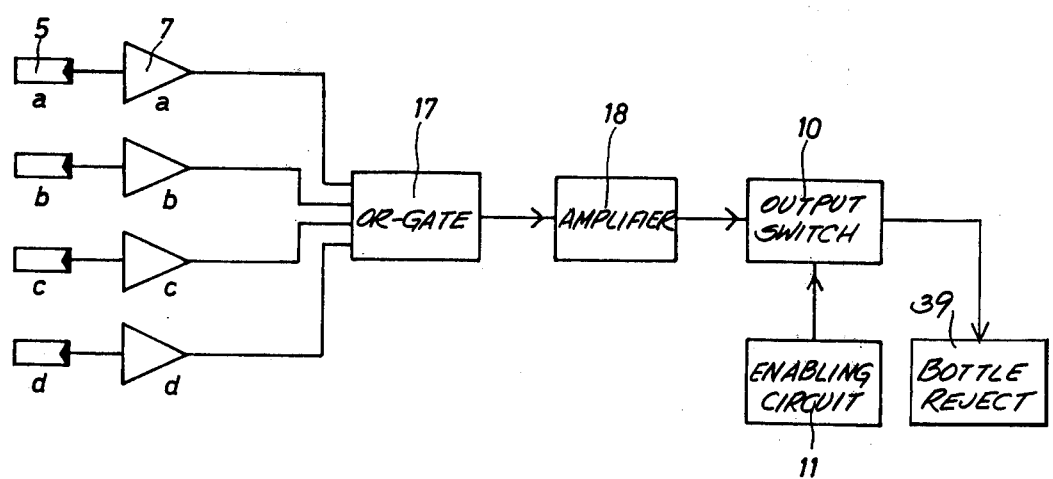
FIG. 7 is a schematic diagram of a modified embodiment of a circuit for monitoring the output of the sensors.

A modified embodiment of a monitoring circuit is shown in FIG. 7 and includes pre-amplifiers 7a, b, c and d connected to the outputs of the sensors 5a, b, c and d. The outputs of the pre-amplifiers 7a, b, c and d are connected to an OR-gate circuit 17 which isolates the outputs from the pre-amplifiers. The OR-gate circuit 17 will provide an output pulse to the output switch 10 through amplifier 18 if the voltage from any of the pre-amplifiers is above or below a certain normal value caused by an increase or decrease of reflected light. The output switch 10 is adjustable so that an amplified signal of a predetermined variance above or below a pre-selected value will actuate the switch 10 to provide energization to the bottle sorting device. The circuit in FIG. 7 also includes an enabling circuit 11 as described above, to enable the output switch only at the appropriate time.

A further modified embodiment of monitoring circuit is shown in FIG. 8 which sequentially compares the outputs from any two sensors 5 and provides a fault or defect indicating signal only when the difference between the two signals from two sensors exceeds a preselected signal value.

The outputs of all the sensors are connected to the input of two shift registers or stepping switches 60 and 62. For the purpose of illustration, only the outputs of the sensors 5a and 5b are connected to both switches 60, 62. A clock pulse generator 14 is coupled to both stepping switches 60, 62 to sequentially enable both switches 60, 62 to transfer the output signals of only two sensors 5 at a time to an operational amplifier 66. For instance, if the outputs from sensors 5a and 5b are simultaneously coupled through the switches 60, 62 to the two input terminals of the operational amplifier for comparison, a difference in voltage level at the two input terminals will result in a signal to the output switch, which can actuate a sorting device 39. If the output signals from sensors 5a and 5b are the same, the operational amplifier will have no output. Minor flaws are easily detected by comparing the outputs of adjacent sensors.

The circuit can be wired so that the output of any combination of two sensors can be compared. For instance, the output of 5a could be compared with 5c or 5d rather than 5b. The advantage of the FIG. 8 circuit is that a general threshold level for a normal bottle does not have to be determined for the output switch. However, either the operational amplifier 66 or the output switch can have a threshold so that only voltage differences reaching a certain level indicating a major flaw will cause the sorting device 39 to be actuated.

As used in the specification and claims, "light" means any source of radiant energy.

Although various embodiments of sensing heads and circuitry are disclosed herein, the object of the invention is to provide improved results in detecting flaws using a substantial number of sensors. Reducing the size of individual sensors results in minor flaws having a significant effect on the output signal for a single small sensor. Thus, minor flaws are more readily detected than with one large sensor. Furthermore, using a plurality of sensors results in a differential output between sensors so that the outputs of the sensors can be compared.

I claim:

1. Inspection apparatus for detecting flaws and defects in containers comprises conveying means for moving containers in a path through an inspection zone, a stationary light sensing head associated with the inspection zone, said sensing head containing a plurality of light sensors arranged around an aperture and forming a continuous 360° sensing screen having a sensing surface larger than the area of the container surface being inspected to afford bottle inspection during bottle movement, a light source associated with said sensing head to provide a light beam through said aperture larger than the area of the container to be inspected for simultaneous reflection from the entire container surface being inspected to said sensing surface and output circuit means coupled to said sensors to sequentially scan each of said sensors as the container moves through the inspection zone and while said container is in said light beam and provide an output signal indicating a container defect.

2. Apparatus in accordance with claim 1 wherein said output circuit means comprises a pre-amplifier for each of said photosensitive sensors, first circuit means coupling said pre-amplifiers to an amplifier, second circuit means for sequentially enabling said first circuit to sequentially apply signals from each of said pre-amplifiers to said amplifier, and an output switch coupled to said amplifier, said output switch being operable in response to signals from said amplifier which vary from a pre-determined normal signal value.

3. Apparatus in accordance with claim 1 wherein said output circuit means includes first circuit means to sequentially compare the output signals of two of said sensors and provide an output signal equal to the difference between the compared signals and an output switch coupled to said first circuit means and adapted to be energized when the output signal attains a preselected value.

4. Apparatus in accordance with claim 1 wherein said output circuit means comprises a pre-amplifier for each of said sensors, an OR-gate circuit coupled to the output of each of said pre-amplifiers, an amplifier coupled to said OR-gate, and an output switch coupled to said amplifier, said output switch being operable in response to signals from said amplifier above and below a predetermined normal signal value.

5. Apparatus in accordance with claim 4 including sorting means for removing defective bottles from the bottle conveying path, and an enabling circuit connected to said output switch to enable said output switch to actuate said sorting means in timed sequence with an inspection cycle.

6. Apparatus in accordance with claim 1 wherein said sensors have a light receiving surface in the form of circular ring sectors, said sectors being circumferentially arranged around said central aperture to provide a complete peripheral scan of the container's rim.

7. Apparatus in accordance with claim 6 wherein said sensors are supported on a platen and wherein said pre-amplifiers for each of said photosensitive sensors are supported on said platen.

8. Apparatus in accordance with claim 7 including voltage adjustment means for each of said devices supported on said platen.

9. Inspection apparatus in accordance with claim 1 wherein said output circuit means includes circuit means coupled to said sensors for sequentially comparing the outputs of groups of two of said sensors and providing an output signal equal to the difference between the outputs of said sensors in said groups.

10. The apparatus of claim 9 in which said plurality of sensors are arranged in a mosaic pattern about a central light source being directed at one side of the pattern and beamed through the aperture and the container being on the other side of the pattern to receive the beam and reflect it back to the mosaic pattern of sensors.

11. Apparatus in accordance with claim 10 wherein said sensors are supported on a flat surface.

12. Apparatus in accordance with claim 10 wherein said sensors are supported on a conical surface.

13. Apparatus in accordance with claim 10 wherein said sensors are supported on a cylindrical surface.

14. Inspection apparatus for detecting defects in the rim of a bottle comprising means for continuously moving bottles through an inspection zone, a stationary light sensing head containing a plurality of relatively small light sensors arranged around an aperture and providing a continuous sensing screen for continuously receiving light from an arc of 360°, a light source providing a beam of light through said aperture for reflection to said sensors, said sensors providing a sensing area larger than the beam of reflected light to afford slight movement of the bottle during inspection, and circuit means coupled to said photosensitive sensors to individually monitor signals from each of said photosensitive sensors while the bottle rim is in registry with said light beam and sense for each of said sensors a preselected variance in signal level from a predetermined normal value indicating a bottle defect to actuate an output switch when a signal of the preselected variance is sensed.

15. Inspection apparatus for detecting minor flaws in the rims of containers, said apparatus comprising a stationary light source for flooding the surface to be inspected, a stationary sensing head containing a plurality of light sensors arranged to simultaneously receive light from the entire surface being inspected, with each sensor receiving only a minor increment of the total reflected light, circuit means coupled to said sensors for monitoring the light received from each sensor including an individual pre-amplifier for each of said sensors, circuit means coupling said pre-amplifiers to an amplifier and an output switch coupled to said amplifier and operable to provide an output signal if the output from any one of said sensors varies a predetermined amount from a signal value for a normal container.

* * * * *